United States Patent [19]

Alig et al.

[11] 4,202,841
[45] May 13, 1980

[54] D-HOMOPREGNANES

[75] Inventors: Leo Alig, Kaiseraugst; Andor Fürst, Basel; Marcel Müller, Frenkendorf, all of Switzerland; Ulrich Kerb, Berlin, Fed. Rep. of Germany; Klaus Kieslich, Berlin, Fed. Rep. of Germany; Rudolf Wiechert, Berlin, Fed. Rep. of Germany

[73] Assignee: Hoffmann-La Roche Inc., Nutley, N.J.

[21] Appl. No.: 973,336

[22] Filed: Dec. 26, 1978

Related U.S. Application Data

[63] Continuation of Ser. No. 827,758, Aug. 25, 1977, abandoned.

[51] Int. Cl.$^2$ .................. C07C 49/00; C07J 63/00
[52] U.S. Cl. ..................... 424/311; 424/331; 424/308; 560/107; 560/257; 568/372
[58] Field of Search .................. 260/586 E; 424/331, 424/308, 311; 560/257, 107

[56] References Cited

U.S. PATENT DOCUMENTS

| 2,860,158 | 11/1958 | Clinton | 260/586 E |
| 3,939,193 | 2/1976 | Alig et al. | 260/586 E |
| 4,026,918 | 5/1977 | Fürst et al. | 260/488 B |
| 4,026,923 | 5/1977 | Alig et al. | 260/488 B |

FOREIGN PATENT DOCUMENTS 1365469  9/1974  United Kingdom ............... 260/586 E

*Primary Examiner*—Paul J. Killos

*Attorney, Agent, or Firm*—Jon S. Saxe; George M. Gould; James H. Callwood

[57] ABSTRACT

D-Homopregnanes of the formula

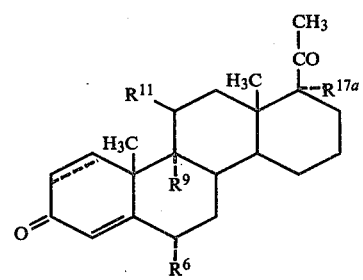

wherein the dotted line in the 1,2-position together with the corresponding solid line denotes a single or double carbon-carbon bond; $R^6$ is hydrogen, fluoro, chloro or methyl; $R^9$ is hydrogen, fluoro, chloro or bromo; $R^{11}$ is hydroxyl, acyloxy, fluoro or chloro; and $R^{17a}$ is hydroxyl or acyloxy with the proviso that when $R^9$ is fluoro, chloro or bromo and $R^{11}$ is fluoro or chloro, the atomic number of $R^{11}$ is less than or equal to that of $R^9$; and with the further proviso that when $R^6$ is hydrogen, and $R^{11}$ and $R^{17a}$ are hydroxy or when $R^6$ is fluoro, $R^{11}$ and $R^{17a}$ are hydroxyl and the dotted line in the 1,2-position together with the corresponding solid line denotes a single carbon-carbon bond, $R^9$ is fluoro, chloro or bromo and processes for the preparation thereof are disclosed.

10 Claims, No Drawings

D-HOMOPREGNANES

This is a continuation of application Ser. No. 827,758 filed Aug. 25, 1977, now abandoned.

The D-homopregnanes of the present invention are useful as anti-inflammatory agents.

Also disclosed are pharmaceutical preparations having anti-inflammatory activity and containing a D-homopregnane of the formula

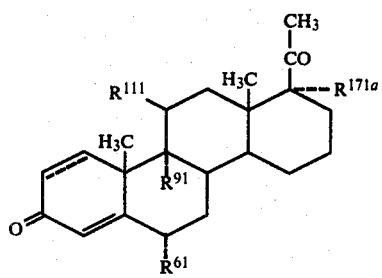

wherein the dotted line in the 1,2-position together with the corresponding solid line denotes a single or double carbon-carbon bond; $R^{61}$ is hydrogen, fluoro, chloro or methyl; $R^{91}$ is hydrogen, fluoro, chloro or bromo; $R^{171a}$ is hydroxyl or acyloxy and $R^{111}$ is hydroxyl, acyloxy, fluoro or chloro with the proviso that when $R^{91}$ is fluoro, chloro or bromo and $R^{111}$ is fluoro or chloro, the atomic number of $R^{111}$ is less than or equal to that of $R^{91}$ as the essential active ingredient.

DESCRIPTION OF THE INVENTION

The present invention relates to D-homopregnanes. More particularly, the invention is concerned in one aspect with D-homopregnanes exhibiting anti-inflammatory activity and with a process for the preparation thereof. The invention is concerned in another aspect with pharmaceutical preparations containing D-homopregnanes and exhibiting anti-inflammatory activity as well as a process for the manufacture of the pharmaceutical preparation.

In accordance with the present invention it has been found that D-homopregnanes of the formula

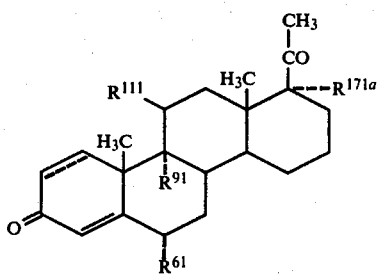

wherein the dotted line in the 1,2-position together with the corresponding sold line denotes a single or double carbon-carbon bond; $R^{61}$ is hydrogen, fluoro, chloro or methyl; $R^{91}$ is hydrogen, fluoro, chloro or bromo; $R^{171a}$ is hydroxyl or acyloxy and $R^{111}$ is hydroxyl, acyloxy, fluoro or chloro with the proviso that when $R^{91}$ is fluoro, chloro or bromo and $R^{111}$ is fluoro or chloro, the atomic number of $R^{111}$ is less than or equal to that of $R^{91}$ have anti-inflammatory activity.

In one aspect, the present invention is based on the foregoing finding and is concerned with pharmaceutical preparations having anti-inflammatory activity and containing as essential active ingredient a D-homopregnane of formula I', and with a process for the manufacture of these pharmaceutical preparations, which process comprises mixing a D-homopregnane of formula I' as essential active ingredient with a pharmaceutically acceptable carrier material.

The following D-homopregnanes of formula I' are known, the preparation thereof being described in British Patent Specification No. 1,365,469:

11β,17aα-dihydroxy-D-homopregn-4-ene-3,20-dione;

11β,17aα-dihydroxy-D-homopregna-1,4-diene-3,20-dione; and

6α-fluoro-11β,17aα-dihydroxy-D-homopregn-4-ene-3,20-dione.

Among the D-homopregnanes of formula I', those of the formula

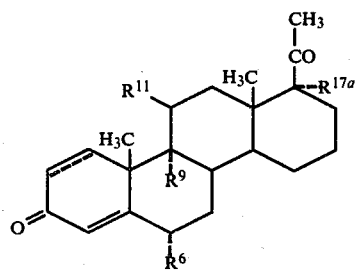

wherein the dotted line in the 1,2-position together with the corresponding solid line denotes a single or double carbon-carbon bond; $R^6$ is hydrogen, fluoro, chloro or methyl; $R^9$ is hydrogen, fluoro, chloro or bromo; $R^{11}$ is hydroxyl, acyloxy, fluoro or chloro and $R^{17a}$ is hydroxyl or acyloxy with the proviso that when $R^9$ is fluoro, chloro or bromo and $R^{11}$ is fluoro or chloro, the atomic number of $R^{11}$ is less than or equal to that of $R^9$; and with the further proviso that when $R^6$ is hydrogen, and $R^{11}$ and $R^{17a}$ are hydroxyl or when $R^6$ is fluoro, $R^{11}$ and $R^{17a}$ are hydroxyl and the dotted line in the 1,2-position together with the corresponding solid line denotes a single carbon-carbon bond, $R^9$ is fluoro, chloro or bromo are novel and, together with a process for their preparation, also form another aspect of the present invention.

As used throughout the specification and appended claims, the term "acyloxy" denotes the residue obtained by removal of the hydroxyl portion of a saturated or unsaturated aliphatic carboxylic acid, a cycloaliphatic, araliphatic or an aromatic carboxylic acid preferably containing up to 15 carbon atoms. Examples of such acids are formic acid, acetic acid, trifluoroacetic acid, pivalic acid, propionic acid, butyric acid, valeric acid, caproic acid, oenanthic acid, undecylenic acid, oleic acid, cyclopentylpropionic acid, cyclohexylpropionic acid, phenylacetic acid and benzoic acid. Especially preferred acyloxy groups are alkanoyloxy groups derived by removal of the hydroxyl portion of alkanecarboxylic acids containing from 1 to 7 carbon atoms such as formic acid, acetic acid, pivalic acid, propionic acid, butyric acid, valeric acid, caproic acid, oenanthic acid and the like.

In the formulas presented herein the various substituents are illustrated as joined to the steroid nucleus by one of two notations: a solid line (—) indicating a substituent which is in the β-orientation (i.e., above the plane of the molecule) and a broken line (- - - -) indicating a substituent which is in the α-orientation (i.e., below the plane of the molecule). The formulas have all been drawn to show the compounds in their absolute stereochemical configuration. Inasmuch as the starting materials, as well as the final products, are derived from naturally occurring materials, they exist in the single absolute configuration depicted herein. The processes of the present invention, however, are intended to apply as well to the synthesis of steroids of the racemic series.

A preferred group D-homopregnanes of formula I comprises those in which $R^{11}$ is hydroxyl. Moreover, those D-homopregnanes of formula I in which $R^9$ is hydrogen, fluoro or chloro are preferred. D-Homopregnanes of formula I containing a double bond in the 1,2-position are also preferred.

Examples of D-homopregnanes of formula I provided by the present invention are:
  11β-butyryloxy-17aα-hydroxy-D-homopregna-1,4-diene-3,20-dione;
  11β-trifluoroacetoxy-17aα-hydroxy-D-homopregna-1,4-diene-3,20-dione;
  17aα-butyryloxy-11β-trifluoroacetoxy-D-homopregna-1,4-diene-3,20-dione;
  17aα-butyryloxy-11β-hydroxy-D-homopregna-1,4-diene-3,20-dione;
  6α-fluoro-11β,17aα-dihydroxy-D-homopregna-1,4-diene-3,20-dione;
  6α-chloro-11β,17aα-dihydroxy-D-homopregna-1,4-diene-3,20-dione;
  6α-fluoro-17aα-hydroxy-11β-trifluoroacetoxy-D-homopregna-1,4-diene-3,20-dione;
  17aα-butyryloxy-6α-fluoro-11β-trifluoroacetoxy-D-homopregna-1,4-diene-3,20-dione;
  17aα-butyryloxy-6α-fluoro-11β-hydroxy-D-homopregna-1,4-diene-3,20-dione;
  17aα-valeroyloxy-6α-chloro-11β-hydroxy-D-homopregna-1,4-diene-3,20-dione;
  9α-fluoro-11β,17aα-dihydroxy-D-homopregna-1,4-diene-3,20-dione;
  9α-chloro-11β,17aα-dihydroxy-D-homopregna-1,4-diene-3,20-dione;
  9α-bromo-11β,17aα-dihydroxy-D-homopregna-1,4-diene-3,20-dione;
  9α-fluoro-17aα-hydroxy-11β-propionyloxy-D-homopregna-1,4-diene-3,20-dione;
  17aα-butyryloxy-9α-fluoro-11β-propionyloxy-D-homopregna-1,4-diene-3,20-dione;
  9α-fluoro-17aα-hydroxy-11β-trifluoroacetoxy-D-homopregna-1,4-diene-3,20-dione;
  17aα-butyryloxy-9α-fluoro-11β-trifluoroacetoxy-D-homopregna-1,4-diene-3,20-dione;
  17aα-butyryloxy-9α-fluoro-11β-hydroxy-D-homopregna-1,4-diene-3,20-dione;
  9α-chloro-11β-hydroxy-17aα-propionyloxy-D-homopregna-1,4-diene-3,20-dione;
  9α-chloro-11β-fluoro-17aα-hydroxy-D-homopregna-1,4-diene-3,20-dione;
  17aα-butyryloxy-9α-chloro-11β-fluoro-D-homopregna-1,4-diene-3,20-dione;
  11β,17aα-dihydroxy-6α-methyl-D-homopregn-4-ene-3,20-dione;
  17aα-butyryloxy-11β-hydroxy-6α-methyl-D-homopregn-4-ene-3,20-dione;
  11β,17aα-dihydroxy-6α-methyl-D-homopregna-1,4-diene-3,20-dione;
  17aα-butyryloxy-11β-hydroxy-6α-methyl-D-homopregna-1,4-diene-3,20-dione;
  6α-methyl-11β,17aα-dipropionyloxy-D-homopregna-1,4-diene-3,20-dione;
  9α-fluoro-11β,17aα-dihydroxy-6α-methyl-D-homopregn-4-ene-3,20-dione;
  17aα-butyryloxy-9α-fluoro-11β-hydroxy-6α-methyl-D-homopregn-4-ene-3,20-dione;
  9α-fluoro-11β,17aα-dihydroxy-6α-methyl-D-homopregna-1,4-diene-3,20-dione;
  9α-fluoro-11β-hydroxy-6α-methyl-17aα-valeroyloxy-D-homopregna-1,4-diene-3,20-dione;
  11β,17aα-dibutyryloxy-9α-chloro-6α-methyl-D-homopregna-1,4-diene-3,20-dione;
  9α-chloro-6α-fluoro-11β,17aα-dihydroxy-D-homopregna-1,4-diene-3,20-dione;
  6α,9α-difluoro-11β,17aα-dihydroxy-D-homopregna-1,4-diene-3,20-dione;
  6α,9α-difluoro-11β-hydroxy-17aα-propionyloxy-D-homopregna-1,4-diene-3,20-dione;
  6α-chloro-9α-fluoro-11β,17aα-divaleroyloxy-D-homopregna-1,4-diene-3,20-dione;
  9α-chloro-11β-fluoro-17aα-hydroxy-6α-methyl-D-homopregna-1,4-diene-3,20-dione;
  9α-chloro-11β-fluoro-6α-methyl-17aα-valeroyloxy-D-homopregna-1,4-diene-3,20-dione;
  9α,11β-dichloro-6α-methyl-17aα-propionyloxy-D-homopregn-4-ene-3,20-dione;
  9α-chloro-6α,11β-difluoro-17aα-hydroxy-D-homopregna-1,4-diene-3,20-dione;
  17aα-butyryloxy-9α-chloro-6α,11β-difluoro-D-homopregna-1,4-diene-3,20-dione;
  6α,9α,11β-trichloro-17aα-hydroxy-D-homopregna-1,4-diene-3,20-dione;
  6α,9α-dichloro-11β-fluoro-17aα-valeroyloxy-D-homopregna-1,4-diene-3,20-dione.

The D-homopregnanes of formula I are prepared in accordance with the present invention by
  (a) hydroxylating a D-homopregnane of the formula

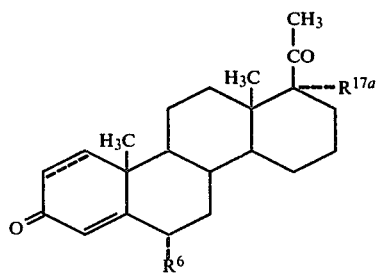

II wherein $R^6$ and $R^{17}$ are as above in the 11-position by means of microorganisms or enzymes produced therefrom, or
  (b) replacing the iodine atom in a D-homopregnane of the formula

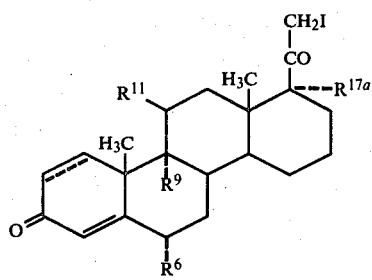

III wherein $R^6$, $R^{11}$ and $R^{17a}$ are as above by a hydrogen atom, or (c) dehydrogenating a D-homopregnane of formula I wherein the dotted line in the 1,2-position together with the corresponding solid line denotes a single carbon-carbon bond and $R^6$, $R^9$, $R^{11}$ and $R^{17a}$ are as above in the 1,2-position, or (d) adding chlorine, chlorine monofluoride, bromine monofluoride, bromine monochloride, hypochlorous or hypobromous acid to the 9,11-double bond of a D-homopregnane of the formula

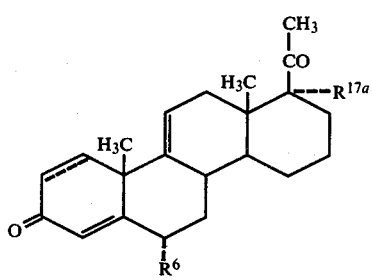

IV wherein $R^6$ and $R^{17a}$ are as above or (e) treating a D-homopregnane of the formula

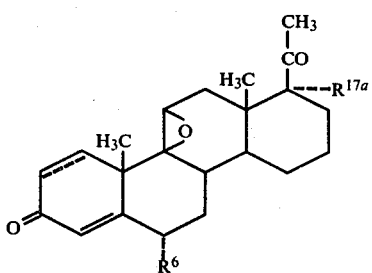

V wherein $R^6$ and $R^{17a}$ are as above with hydrogen fluoride, hydrogen chloride or hydrogen bromide, or (f) saponifying an acyloxy group in a D-homopregnane of formula I wherein $R^6$ and $R^9$ are as above and at least one of $R^{17a}$ and $R^{11}$ is an acyloxy group, or (g) isomerizing a 6β-substituted-D-homopregnane of the formula

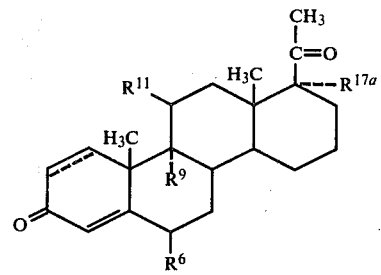

I″ wherein $R^6$ is chloro, fluoro or methyl, $R^9$, $R^{11}$ and $R^{17a}$ are as above and $R^6$ occupies the β-position to the corresponding 6α-isomer, or (h) fluorinating or chlorinating a D-homopregnane of the formula

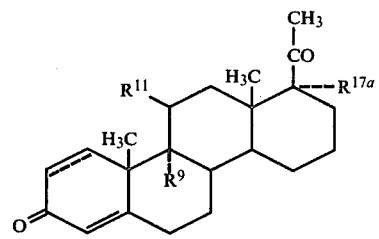

VI wherein $R^9$, $R^{11}$ and $R^{17a}$ are as above in the 6-position, or (i) acylating an 11β- or 17aα-hydroxy group in a D-homopregnane of formula I wherein $R^6$ and $R^9$ are as above and at least one of $R^{11}$ and $R^{17a}$ is hydroxyl, or (j) oxidizing and isomerizing the 3-hydroxy-Δ$^5$-group in a D-homopregnane of the formula

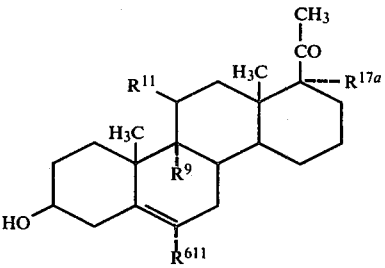

VIII wherein $R^{611}$ is hydrogen or methyl and $R^9$, $R^{11}$ and $R^{17a}$ are as above to the 3-keto-Δ$^4$-group, or (k) reducing the 11-keto group in a D-homopregnane of the formula

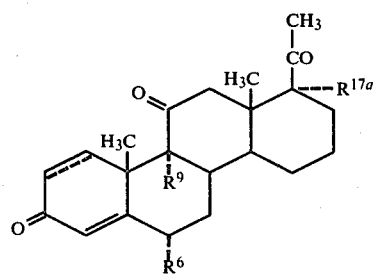

IX wherein $R^6$, $R^9$ and $R^{17a}$ are as above to the hydroxyl group with prior protection of the 3- and 20-keto groups and subsequent removal of the protecting groups, or (l) oxidizing the 17a(20)-double bond of a D-homopregnane of the formula

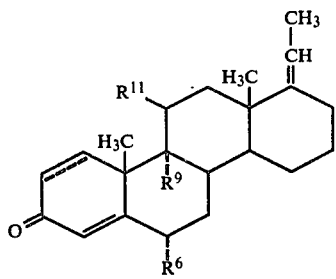

wherein $R^6$, $R^9$ and $R^{11}$ are as above to the 17aα-hydroxy-20-keto group, or (m) methylating a D-homopregnane of formula VI wherein $R^9$, $R^{11}$ and $R^{17a}$ are as above in the 6-position, or (n) converting the 17β-ethynyl group in a D-homopregnane of the formula

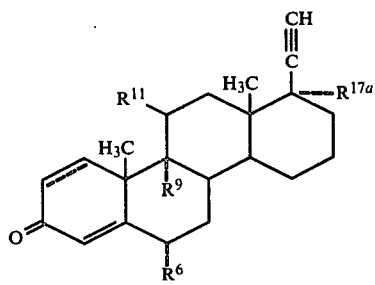

wherein $R^6$, $R^9$, $R^{11}$ and $R^{17a}$ are as above into the acetyl group, or (o) dehydrogenating a D-homopregnane of the formula

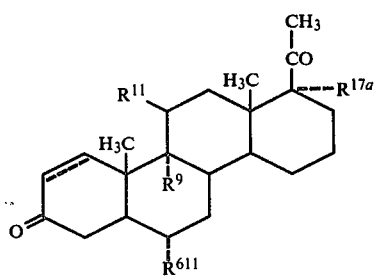

wherein $R^{6ΙΙ}$, $R^9$, $R^{11}$ and $R^{17a}$ are as above in the 4-position.

The hydroxylation of a D-homopregnane of formula II in accordance with embodiment (a) of the process can be carried out according to methods known per se for the microbial 11-hydroxylation of steroids. For this 11-hydroxylation there can be used microorganisms of the taxonomic groups Fungi and Schizomycetes, especially of the sub-groups Ascomycetes, Phycomycetes, Basidiomycetes and Actinomycetales. There can also be used mutants produced in a chemical manner (e.g., by treatment with nitrite) or in a physical manner (e.g., by irradiation) as well as cell-free enzyme preparations obtained from the microorganisms. Especially suitable microorganisms for the 11β-hydroxylation are those of the genera Curvularia (e.g., C. lunata NRRL 2380 and NRRL 2178; ATCC 13633, 13432, 14678, IMI 77007, IFO 2811), Absidia (e.g., A. coerula IFO 4435), Colletotrichum (e.g., C. pisi ATCC 12520), Pellicolaria (e.g., P. filamentosa IFO 6675), Streptomyces (e.g., S. fradiae ATCC 10745), Cunninghamella (e.g., C. bainieri ATCC 9244, C. verticellata ATCC 8983, C. elegans NRRL 1392 and ATCC 9245, C. blakesleeana ATCC 8688, 8688a, 8688b, 8983 and C. echinulata ATCC 8984), Pycnosporium (e.g., sp. ATCC 12231), Verticillium (e.g., V. theobromae CBS 39858), Aspergillus (e.g., A. quadrilieatus JAM 2763), Trichothecium (e.g., T. roseum ATCC 12519) and Phoma (e.g., sp. ATCC 13145).

The replacement of the iodine atom in a D-homopregnane of formula III by a hydrogen atom in accordance with embodiment (b) of the process can be carried out by treatment with a reducing agent such as sodium hydrogen sulfite.

The 1,2-dehydrogenation of a 1,2-saturated D-homopregnane of formula I in accordance with embodiment (c) of the process can be carried out by methods known per se such as, for example, by microbiological methods or by the use of a dehydrogenating agent such as iodine pentoxide, periodic acid, selenium dioxide, 2,3-dichloro-5,6-dicyanobenzoquinone, chloranil or lead tetraacetate. Suitable micro-organisms for the 1,2-dehydrogenation are, for example, Schizomycetes, especially those of the genera Arthrobacter (e.g., A. simplex ATCC 6946), Bacillus (e.g., B. lentus ATCC 13805 and B. sphaericus ATCC 7055), Pseudomonas (e.g., P. aeruginosa IFO 3505), Flavobacterium (e.g., F. flavenscens IFO 3058), Lactobacillus (e.g., L. vrevis IFO 3345) and Nocardia (e.g., N.opaca ATCC 4276).

In carrying out embodiments (d) and (e) of the process, a D-homopregnane of formula IV or V is conveniently dissolved in a suitable solvent (e.g., an ether such as tetrahydrofuran or dioxane, a chlorinated hydrocarbon such as methylene chloride or chloroform, or a ketone such as acetone) and allowed to react with the reagent which is added thereto. Hypochlorous or hypobromous acid is conveniently generated in situ; for example, from N-bromo- or N-chloroamides or imides such as N-chlorosuccinimide or N-bromoacetamide and a strong acid, preferably perchloric acid. Embodiment (e) is preferred for the preparation of 9-fluoro-11-hydroxy-D-homopregnanes of formula I.

The saponification of an acyloxy group in a D-homopregnane of formula I in accordance with embodiment (f) of the process can be carried out by methods known per se; for example, by aqueous-methanolic potassium carbonate solution or sodium hydrogen carbonate solution.

The isomerization of a 6β-(fluoro, chloro or methyl)-D-homopregnane of formula I", especially a 6β-(fluoro or chloro)-D-homopregnane, in accordance with embodiment (g) of the process can be carried out by treatment with an acid, especially a mineral acid, such as hydrochloric acid, in a solvent (e.g., dioxane or glacial acetic acid).

The fluorination or chlorination of a D-homopregnane of formula VI in the 6-position in accordance with embodiment (h) of the process can be carried out by methods known per se. A 6,7-saturated D-homopregnane of formula VI can be fluorinated or chlorinated by reaction with a fluorinating or chlorinating agent such as a N-chloroamide or imide (e.g., N-chlorosuccinimide) or with elemental chlorine [see J. Am. Chem. Soc., 72, 4534 (1950)]. This embodiment of the process is preferably carried out by converting a 6,7-saturated D-homopregnane of formula VI into a 3-enol ester or 3-enol ether (e.g., the 3-enol acetate) and reacting the 3-enol ester or 3-enol ether with chlorine [see J. Am. Chem. Soc., 82, 1230 (1960)], with a N-chloroimide [see J. Am. Chem. Soc., 82, 1230 (1960); 77, 3827 (1955)] or with perchloryl fluoride [see J. Am. Chem. Soc., 81, 5259 (1959); Chem. and Ind., 1959, 1317]. Trifluoromethylhypofluorite can also be used as the fluorinating agent.

Insofar as the previously described fluorination or chlorination yields an isomer mixture (i.e., a mixture of 6α- and 6β-(fluoro or chloro)-D-homopregnanes, the mixture can be separated into the pure isomers according to known methods such as chromatography.

The acylation of an 11β- and/or 17aα-hydroxy group in a D-homopregnane of formula I in accordance with embodiment (i) of the process can be carried out by methods known per se; for example, by treatment with an acylating agent such as an acyl chloride or anhydride in the presence of an acid binding agent (e.g., pyridine or triethylamine) and a suitable catalyst (e.g., p-dimethylaminopyridine) or in the presence of a strong acid catalyst (e.g., p-toluenesulfonic acid). As the solvent for the acylation there may be mentioned organic solvents which do not contain hydroxyl groups (e.g., chlorinated hydrocarbons such as methylene chloride or hydrocarbons such as benzene). When the acylation is carried out in basic medium in the presence of p-dimethylaminopyridine, then the 11β-hydroxy group can be selectively acylated in the presence of the 17aα-hydroxy group.

The oxidation of the 3-hydroxy-Δ$^5$-group in a D-homopregnane of formula VIII in accordance with embodiment (j) of the process can be carried out according to the Oppenauer procedure (e.g., using aluminum isopropylate) or by means of oxidizing agents such as chromium trioxide (e.g., Jones' reagent) or according to the Pfitzner-Moffatt procedure using dimethylsulfoxide/dicyclohexylcarbodiimide (the initially obtained Δ$^5$-3-ketone requiring subsequent isomerization to the Δ$^4$-3-ketone) or by means of pyridine/sulfur trioxide.

In carrying out embodiment (k) of the process, the keto groups in the 3- and 20-positions of a D-homopregnane of formula IX are first protected (e.g., as the semicarbazone). Where a 1,2-double bond is present, the 3-keto group can also be protected by the formation of an enamine. The protecting groups can subsequently be removed by acid hydrolysis. A Δ$^{1,4}$-3-ketone can also be converted into a Δ$^{1,3,5}$-3-enamine using a secondary amine in the presence of titanium tetrachloride. The reduction of the 11-keto group of a thus-protected D-homopregnane can be carried out using a complex metal hydride such as lithium aluminum hydride, sodium borohydride or diisobutyl aluminum hydride.

The oxidation of the 17(20)-double bond in a D-homopregnane of formula X in accordance with embodiment (l) of the process can be carried out, for example, with an oxidizing agent such as a tertiary amine N-oxide peroxide in tert. butanol/pyridine in the presence of catalytic amounts of osmium tetroxide. Examples of tertiary amine N-oxide peroxides which can be used in this embodiment are N-methylmorpholine N-oxide peroxide and triethylamine oxide peroxide. The 17(20)-double bond can also be oxidized with an oxidizing agent such as osmium tetroxide or permanganate to give a 17,20-glycol which can be further oxidized to the 17aα-hydroxy-2-ketone with an oxidizing agent such as chromic acid.

The methylation of a D-homopregnane of formula VI in the 6-position in accordance with embodiment (m) of the process can be carried out, for example, by converting a D-homopregnane of formula VI into a 3-enol ether (e.g., by treatment with an orthoformic acid ester such as ethyl orthoformate in the presence of an acid such as p-toluenesulfonic acid, if desired, with addition of the corresponding alcohol; or by treatment with a dialkoxypropane such as 2,2-dimethoxypropane in methanol/dimethylformamide in the presence of p-toluenesulfonic acid) and reacting the 3-enol ether with a tetrahalomethane (e.g., carbontetrabromide, dibromodichloromethane or bromotrichloromethane) to give a trihalomethyl-Δ$^4$-3-ketone. The trihalomethyl-Δ$^4$-3-ketone can be dehydrohalogenated with a base such as collidine to give a dihalomethylene-Δ$^4$-3-ketone which can be converted by catalytic hydrogenation under mild conditions (e.g., using a Pd/SrCO$_3$ catalyst) into a 6α-methyl-Δ$^4$-3-ketone.

Another methylation procedure consists in converting a 1,2-saturated D-homopregnane of formula VI into a 3-enol ether as described earlier and reacting this 3-enol ether by methods known per se to give the corresponding 6-formyl derivative, reducing the formyl group with sodium borohydride to the hydroxymethyl group and finally dehydrating the product obtained with cleavage of the enol ether, there being obtained a 6-methylene-D-homopregnane of the formula

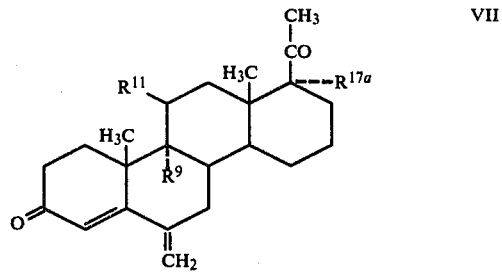

VII wherein R$^9$, R$^{11}$ and R$^{17a}$ are as above.

6-Methylene-D-homopregnanes of formula VII can also be obtained by converting a 1,2-saturated D-homopregnane of formula VI into a 3-enamine with formaldehyde and dehydrating the hydroxymethylation product using an acid such as p-toluenesulfonic acid.

A 6-methylene-D-homopregnane of formula VII can be catalytically hydrogenated to give a corresponding 6-methyl-D-homopregnane of formula I by methods known per se; for example, using a known hydrogenation catalyst.

The conversion of the 17β-ethynyl group in a D-homopregnane of formula XI into the acetyl group in accordance with embodiment (n) of the process can be carried out in the presence of a suitable catalyst such as p-toluenesulfonamide-mercury or with acid ion exchangers activated with mercury salts.

In accordance with embodiment (o) of the process, a D-homopregnane of formula XII can be dehydrogenated in the 4-position or 1,4-position by bromination and subsequent dehydrobromination.

The starting materials used in the foregoing processes, insofar as they are not known or insofar as their preparation is not described hereinafter, can be prepared by analogy to known methods or methods described in the Examples hereinafter.

The D-homopregnanes of formula I possess anti-inflammatory activity and can accordingly be used, for example, for the treatment of inflammatory conditions such as eczemas.

In general, pharmaceutical preparations for internal administration can contain 0.01% to 5.0% of a D-homopregnane of formula I. The daily dosage can vary between 0.05 mg. and 10.0 mg. depending on the condition to be treated and the duration of the desired treatment. The amount of D-homopregnane of formula I in topical preparations lies, in general, in the range of from 0.0001 wt.% to 5 wt.%, advantageously in the range of from 0.001 wt.% to 0.5 wt.% and preferably in the range of from 0.01 wt.% to 0.25 wt.%.

The D-homopregnanes of formula I can be used as medicaments in the form of pharmaceutical preparations which contain them in association with a compatible pharmaceutical carrier material. This carrier material can be an organic or inorganic inert carrier material suitable for enteral, percutaneous or parenteral administration such as, for example, water, gelatin, gum arabic, lactose, starch, magnesium stearate, talc, vegetable oils, polyalkyleneglycols, petroleum jelly, etc. The pharmaceutical preparations can be made up, for example, as salves or as solutions, suspensions or emulsions. The pharmaceutical preparations may be sterilized and/or may contain adjuvants such as preserving, stabilizing, wetting or emulsifying agents, salts for the variation of the osmotic pressure or buffers. They can also contain still other therapeutically valuable materials.

The following Examples illustrate the manner in which the D-homopregnanes of formula I can be prepared.

EXAMPLE 1

100 mg. of 11β,17aα-acetoxy-D-homopregn-4-en-20-yn-3-one and 200 mg. of mercury-p-toluenesulfonamide were boiled at reflux for 20 hours in 5 ml. of alcohol. The mixture was poured into dilute hydrochloric acid and extracted three times with methylene chloride. The organic phases were washed with dilute sodium chloride solution, dried and evaporated. Chromatography of the residue on silica gel gave 11β,17aα-diacetoxy-D-homopregn-4-ene-3,20-dione; UV: $\epsilon_{242}=16250$ NMR: signals at

| δ = | 1.08 ppm (S) 3H | } 18-Me,19-Me |
|---|---|---|
| | 1.24 ppm (S) 3H | |
| | 2.02 ppm (S) 3H | } —COCH₃ and 2x-OOCCH₃ |
| | 2.09 ppm (S) 3H | |
| | 2.13 ppm (S) 3H | |
| | 5.47 ppm (m) 1H | H₁₁eq |
| | 5.70 ppm (m) 1H | H₄ |

The starting material can be prepared as follows:

3β,11β,17aα-trihydroxy-D-homopregn-5-en-20-yne is oxidized according to the Oppenauer procedure to give 11β,17aα-dihydroxy-D-homopregn-4-en-20-yn-3-one and this is subsequently converted in acetic acid anhydride and acetic acid in the presence of catalytic amounts of p-toluenesulfonic acid into 11β,17aα-diacetoxy-D-homopregn-4-en-20-yn-3-one.

EXAMPLE 2

1 g. of 11β-acetoxy-6α-fluoro-D-homopregna-4,17a(20)-dien-3-one, 22 ml. of tert.-butanol, 1.5 ml. of pyridine, 4.3 mg. of osmium tetroxide and 5.3 ml. of N-methylmorpholine oxide hydrogen peroxide solution [L. Fieser and M. Fieser, Reagents for Organic Synthesis, page 690 (1967)] were stirred at 25° C. After 24 hours, 2.5 mg. of osmium tetroxide and 3.0 ml. of N-methylmorpholine oxide hydrogen peroxide solution were added. After a further 24 hours, there were added while stirring 20 ml. of 2 N hydrochloric acid, 1.5 g. of thiourea and 50 ml. of methylene chloride. The aqueous phase was separated and extracted twice with methylene chloride. The methylene chloride solutions were washed with water and dilute sodium chloride solution, dried over sodium sulfate and evaporated. Chromatography of the residue on silica gel gave 11β-acetoxy-6α-fluoro-17aα-hydroxy-D-homopregn-4-ene-3,20-dione of melting point 202°-203° C.; UV: $\epsilon_{234}=15900$; $[\alpha]_D=+98°$ (c=0.1% in dioxane).

The starting material can be prepared as follows:

11β-Hydroxy-D-homopregna-4,17a(20)-dien-3-one is converted in ether and acetic acid anhydride in the presence of perchloric acid into 3,11β-diacetoxy-D-homopregna-3,5,17a(20)-triene from which, by treatment with perchloryl fluoride and subsequent isomerization, there is obtained 11β-acetoxy-6α-fluoro-D-homopregna-4,17a(20)-dien-3-one.

EXAMPLE 3

400 mg. of 11β,17aα-diacetoxy-3β-hydroxy-D-homopregn-5-en-20-one were heated to boiling in 5 ml. of cyclohexanone and 30 ml. of toluene. 5 ml. were distilled off. After the addition of 600 mg. of aluminum tri(tert-butylate), the mixture was boiled at reflux under argon for 6 hours. The mixture was poured onto 2 N hydrochloric acid and extracted three times with toluene. The organic phases were washed to neutrality with sodium hydrogen carbonate solution and sodium chloride solution, dried and evaporated. Chromatography of the residue on silica gel gave 11β,17aα-diacetoxy-D-homopregn-4-ene-3,20-dione which was identical with the product obtained according to Example 1.

The starting material can be prepared as follows:

3β,11β-Dihydroxy-D-homoandrost-5-en-17aα-one is reacted at reflux with ethynylmagnesium bromide in tetrahydrofuran. Chromatographical purification of the reaction mixture gives 17aβ-ethynyl-3β,11β,17aα-trihydroxy-D-homoandrost-5-ene of melting point 232°-234° C.; $[\alpha]_D=-77°$ (c=0.1% in dioxane).

From the foregoing 17aβ-ethynyl-3β,11β,17aα-trihydroxy-D-homoandrost-5-ene there is obtained with mercury-p-toluenesulfonamide in boiling alcohol 3β,11β,17aα-trihydroxy-D-homopregn-5-en-20-one of melting point 244°-247° C.; $[\alpha]_D=-101°$ (c=0.1% in dioxane).

The foregoing 3β,11β,17aα-trihydroxy-D-homopregn-5-en-20-one is converted with acetic anhydride and a catalytic amount of perchloric acid in ethyl acetate into 3β,11β,17aα-triacetoxy-D-homopregn-5-en-20-one from which there is obtained by partial saponification with potassium carbonate in methanol 11β,17aα-diacetoxy-3β-hydroxy-D-homopregn-5-en-20-one.

EXAMPLE 4

4.9 g. of 9α-fluoro-11β,17aα-dihydroxy-21-iodo-D-homopregna-1,4-diene-3,20-dione, 80 ml. of ether, 80 ml. of benzene, 40 ml. of water and 40 ml. of saturated sodium hydrogen sulfite solution were stirred at 25° C. for 30 hours. The mixture was diluted with ethyl acetate. The aqueous phase was separated and extracted twice with ethyl acetate. The ethyl acetate solutions were washed twice with sodium chloride solution, dried over sodium sulfate and evaporated. Filtration on silica gel and crystallization from acetone/hexane gave 9α-fluoro-11β,17aα-dihydroxy-D-homopregna-1,4-diene-3,20-dione of melting point 268°–269° C.; UV: $\epsilon_{329}=15200$; $[\alpha]_D=+67°$ (c=0.1% in methanol).

The starting material can be prepared by reacting 9α-fluoro-D-homoprednisolone [melting point 241°–246° C.; $[\alpha]_D=+101°$ (c=0.1% in dioxane); UV: $\epsilon_{238}=14540$] with methanesulfonyl chloride in pyridine to give 9α-fluoro-11β,17aα-dihydroxy-21-methanesulfonyloxy-D-homopregna-1,4-diene-3,20-dione and reacting this with sodium iodide in acetone to give 9α-fluoro-11β,17aα-dihydroxy-21-iodo-D-homopregna-1,4-diene-3,20-dione of melting point 190° C. (decomposition); $[\alpha]_D=+118°$ (c=0.1% in dioxane); UV: $\epsilon_{238}=15750$.

In an analogous manner, from 6α-fluoro-11β,17aα-dihydroxy-21-iodo-D-homopregna-1,4-diene-3,20-dione [melting point 175°–177° C.; UV $\epsilon_{243}=15830$; $[\alpha]_D=+121°$ (c=0.1% in dioxane)] there was obtained 6α-fluoro-11β,17aα-dihydroxy-D-homopregna-1,4-diene-3,20-dione of melting point 183°–184° C.; UV: $\epsilon_{242}=14400$; $[\alpha]_D=+56°$ (c=0.1% in dioxane); and from 6α,9α-difluoro-11β,17aα-dihydroxy-21-iodo-D-homopregna-1,4-dien-3,20-dione [melting point 189°–190° C.; UV: $\epsilon_{238}=16750$; $[\alpha]_D=+115°$ (c=0.1% in dioxane)] there was obtained 6α,9α-difluoro-11β,17aα-dihydroxy-D-homopregna-1,4-diene-3,20-dione of melting point 230°–231° C.; UV: $\epsilon_{238}=16000$; $[\alpha]_D=+57°$ (c=0.1% in dioxane).

EXAMPLE 5

60 mg. of 9,11β-epoxy-17aα-hydroxy-D-homo-9β-pregna-1,4-diene-3,20-dione were stirred at 25° C. for 15 minutes in 1.5 ml. of glacial acetic acid and 0.15 ml. of 37% hydrochloric acid. The mixture was poured into dilute sodium hydrogen carboate solution and extracted three times with methylene chloride. The methylene chloride solutions were washed twice with dilute sodium chloride solution, dried and evaporated. From acetone there was obtained 9α-chloro-11β,17aα-dihydroxy-D-homopregna-1,4-diene-3,20-dione of melting point 265°–270° C. (decomposition); UV: $\epsilon_{240}=15080$; $[\alpha]_D=+94°$ (c=0.1% in dimethylsulfoxide).

EXAMPLE 6

340 mg. of 17aα-hydroxy-D-homopregna-1,4,9(11)-triene-3,20-dione and 330 mg. of N-chlorosuccinimide were stirred at 25° C. for 6 hours in 3.5 ml. of a solution of 1 part of urea and 1 part of hydrogen fluoride. The mixture was poured into water and extracted three times with methylene chloride. The organic phases were washed twice with dilute sodium chloride solution, which contained 1% sodium hydrogen carbonate and 1% sodium sulfite, dried and evaporated. Chromatography on silica gel gave 9α-chloro-11β-fluoro-17aα-hydroxy-D-homopregna-1,4-diene-3,20-dione of melting point 296°–297° C.; $[\alpha]_D=+85°$ (c=0.1% in dioxane); UV: $\epsilon_{238}=15870$.

EXAMPLE 7

100 mg. of 9,11β-epoxy-17aα-hydroxy-D-homo-9β-pregna-1,4-diene-3,20-dione were stirred at 25° C. for 1 hour in 2 ml. of a solution of 1 part of urea and 1.3 parts of hydrogen fluoride. The mixture was poured into water and extracted with methylene chloride as usual. Chromatography of the crude product on silica gel gave 9α-fluoro-11β,17aα-dihydroxy-D-homopregna-1,4-diene-3,20-dione of melting point 268°–269° C.; UV: $\epsilon_{239}=15200$; $[\alpha]_D=+67°$ (c=0.1% in methanol).

The starting material, 9,11β-epoxy-17aα-hydroxy-D-9β-pregna-1,4-diene-3,20-dione [melting point 179°–180° C.; UV: $\epsilon_{248}=16060$; $[\alpha]_D=-15°$ (c=0.1% in dioxane], is obtained from 9β-bromo-11β,17aα-dihydroxy-D-homopregna-1,4-diene-3,20-dione and potassium acetate in alcohol after heating to reflux for several hours.

EXAMPLE 8

170 mg. of 17aα-hydroxy-D-homopregna-1,4,9(11)-triene-3,20-dione and 130 mg. of N-bromoacetamide were treated in 8.2 ml. of dioxane and 1.65 ml. of water with 0.84 ml. of 10% perchloric acid. After 15 minutes, 435 mg. of sodium sulfite were added and the mixture was diluted with water and a large amount of methylene chloride. The aqueous phase was extracted three times with methylene chloride. The methylene chloride solutions were washed twice with dilute sodium chloride solution, dried over sodium sulfate and evaporated. The resulting 9α-bromo-11β,17aα-dihydroxy-D-homopregna-1,4-diene-3,20-dione melted at 215° C. (decomposition). UV:$\epsilon_{242}=14050$; $[\alpha]_D=+91°$ (c=0.09% in dimethylsulfoxide).

The starting material, 17aα-hydroxy-D-homopregna-1,4,9(11)-triene-3,20-dione [melting point 190°–191° C.; UV: $\epsilon_{239}=15500$; $[\alpha]_D=-80°$ (c=0.1% in dioxane)], is obtained from 11β,17aα-dihydroxy-D-homopregna-1,4-diene-3,20-dione by reaction with methanesulfonyl chloride and sulfur dioxide in pyridine and dimethylformamide.

EXAMPLE 9

1 g. of 9α-fluoro-11β,17aα-dihydroxy-D-homopregna-1,4-diene-3,20-dione, 375 mg. of 4-dimethylaminopyridine, 5 ml. of triethylamine and 5 ml. of propionic anhydride were stirred at 25° C. for 2 hours under argon. After the addition of 5 ml. of water, the mixture was stirred for 10 minutes, then poured into 2 N hydrochloric acid and extracted three times with methylene chloride. The methylene chloride solutions were washed to neutrality with water, dried over sodium sulfate and evaporated. Chromatography of the residue on silica gel gave 9α-fluoro-17aα-hydroxy-11β-propionyloxy-D-homopregna-1,4-diene-3,20-dione of melting point 201°–202° C.; UV: $\epsilon_{238}=15500$; $[\alpha]_D=+93°$ (c=0.1% in dioxane).

EXAMPLE 10

490 mg. of 9α-fluoro-17aα-hydroxy-11β-propionyloxy-D-homopregna-1,4-diene-3,20-dione were stirred at 40° C. for 4.5 hours in 5 ml. of butyric acid and 2 ml. of trifluoroacetic acid anhydride. The mixture was poured into 5% aqueous pyridine, acidified after 10 minutes with hydrochloric acid and extracted with methylene chloride. The organic phases were washed to neutrality with sodium hydrogen carbonate solution and dilute sodium chloride solution, dried and evaporated. Chromatography of the residue on silica gel gave 17aα-butyryloxy-9α-fluoro-11β-propionyloxy-D-homopregna-1,4-diene-3,20-dione of melting point 199°–200° C.; UV: $\epsilon_{238}=16550$; $[\alpha]_D=+71°$ (c=1% in dioxane).

In an analogous manner, from 9α-chloro-11β-fluoro-17aα-hydroxy-D-homopregna-1,4-diene-3,20-dione there was obtained 17aα-butyryloxy-9α-chloro-11β-fluoro-D-homopregna-1,4-diene-3,20-dione of melting point 170°-171° C.; UV: $\epsilon_{238} = 15750$; $[\alpha]_D = +43°$ (c=1% in dioxane).

EXAMPLE 11

1 g. of 6-fluoro-11β,17aα-dihydroxy-D-homopregn-4-ene-3,20-dione and 660 mg. of selenium dioxide were stirred at reflux for 24 hours under argon in 50 ml. of tert.-butanol and 0.5 ml. of glacial acetic acid. The mixture was filtered and evaporated. The residue was dissolved in ethyl acetate and washed successively with sodium hydrogen carbonate solution, water, ice-cold ammonium sulfide solution, dilute ammonia, water, dilute hydrochloric acid and water. The ethyl acetate solution was dried over sodium sulfate and evaporated in vacuo. Chromatography on silica gel gave 6α-fluoro-11β,17aα-dihydroxy-D-homopregna-1,4-diene-3,20-dione of melting point 183°-184° C.; UV: $\epsilon_{242} = 14400$; $[\alpha]_D = +56°$ (c=0.1% in dioxane).

EXAMPLE 12

40 mg. of 11β,17aα-dihydroxy-D-homopregna-1,4-diene-3,20-dione, 15 mg. of 4-dimethylaminopyridine, 0.2 ml. of triethylamine and 0.2 ml. of butyric anhydride were stirred at 25° C. for 2 hours under argon. After the addition of 0.2 ml. of water, the mixture was stirred for 10 minutes, then poured into 2 N hydrochloric acid and extracted three times with methylene chloride. The methylene chloride solutions were washed to neutrality with water, dried over sodium sulfate and evaporated. Preparative thin-layer chromatography gave non-crystalline 11β-butyryloxy-17aα-hydroxy-D-homopregna-1,4-diene-3,20-dione. UV: $\epsilon_{242} = 14000$

| NMR: | 1.21 ppm S 3H | $18_{Me}, 19_{Me}$ |
|---|---|---|
| | 1.37 ppm S 3H | |
| | 5.50 ppm m 1H | 11αH |

EXAMPLE 13

1 g. of 11β,17aα-diacetoxy-D-homopregn-4-ene-3,20-dione was dissolved in 10 ml. of ethyl orthoformate and 10 ml. of absolute alcohol and treated with 10 mg. of p-toluenesulfonic acid in 1 ml. of alcohol. After 10 minutes, 2 drops of pyridine were added to the mixture and the resulting mixture was poured into dilute sodium hydrogen carbonate solution and extracted with methylene chloride. The methylene chloride solution was washed with water, dried over sodium sulfate and evaporated to dryness. The crude 3-ethoxy-11β,17aα-dihydroxy-D-homopregna-3,5-dien-20-one was gasified in 40 ml. of dimethylformamide and 4 ml. of water with perchloryl fluoride until the enol ether could no longer be detected in a thin-layer chromatogram. The mixture was evaporated in vacuo and the residue, a mixture of the two isomeric 11,17a diacetoxy-6-fluoro-D-homopregn-4-ene-3,20-diones, left to stand at 25° C. for 30 minutes in 100 ml. of glacial acetic acid and 1 ml. of 33% hydrogen bromide in glacial acetic acid. After the addition of 5 ml. of pyridine, the mixture was evaporated in vacuo. Chromatography of the residue on silica gel gave 11β,17aα-diacetoxy-6α-fluoro-D-homopregn-4-ene-3,20-dione of melting point 236°-237° C.; $[\alpha]_D = +25°$ (c=0.1% in dioxane); UV: $\epsilon_{232} = 16100$.

EXAMPLE 14

1.1 g. of 11β,17aα-dihydroxy-D-homopregna-1,4-diene-3,20-dione were dissolved at −10° C. in 6.2 ml. of pyridine and 0.474 ml. of trifluoroacetic anhydride and stirred at 0° C. for 50 minutes under argon. The mixture was poured into dilute hydrochloric acid and extracted three times with methylene chloride. The methylene chloride solutions were washed to neutrality with sodium hydrogen carbonate solution and sodium chloride solution, dried and evaporated. Chromatography on silica gel gave pure non-crystalline 17aα-hydroxy-11β-trifluoroacetoxy-D-homopregna-1,4-diene-3,20-dione; UV: $\epsilon_{239} = 14200$; $[\alpha]_D = +84°$ (c=0.1% in dioxane).

EXAMPLE 15

1.2 g. of 17aα-hydroxy-11β-trifluoroacetoxy-D-homopregna-1,4-diene-3,20-dione were dissolved in a mixture of 12 ml. of butyric acid and 4.8 ml. of trifluoroacetic anhydride and stirred at 50° C. for 4 hours. The mixture was poured into aqueous pyridine, stirred for 10 minutes, acidified with 2 N hydrochloric acid and extracted three times with methylene chloride. The methylene chloride solutions were washed to neutrality with sodium hydrogen carbonate solution and sodium chloride solution, dried over sodium sulfate and evaporated. Chromatography of the residue on silica gel gave pure 17aα-butyryloxy-11β-trifluoroacetoxy-D-homopregna-1,4-diene-3,20-dione as a foam. UV: $\epsilon_{240} = 13900$; $[\alpha]_D = +41°$ (c=0.1% in dioxane).

EXAMPLE 16

1.1 g. of 17aα-butyryloxy-11β-trifluoroacetoxy-D-homopregna-1,4-diene-3,20-dione were treated in 55 ml. of methanol and 4.2 ml. of water with 4.2 ml. of saturated sodium hydrogen carbonate solution and stirred at 25° C. for 48 hours. The methanol was evaporated and the residue taken up in methylene chloride and water. The methylene chloride solution was washed with dilute sodium chloride solution, dried and evaporated. There was obtained 17aα-butyryloxy-11β-hydroxy-D-homopregna-1,4-diene-3,20-dione as a foam which was pure according to thin-layer chromatography. UV: $\epsilon_{244} = 13940$; $[\alpha]_D = +22°$ (c=0.1% in dioxane).

EXAMPLE 17

In an analogous manner to Examples 14–16, from 9α-fluoro-11β,17aα-dihydroxy-D-homopregna-1,4-diene-3,20-dione there was obtained 17aα-butyryloxy-9α-fluoro-11β-hydroxy-D-homopregna-1,4-diene-3,20-dione of melting point 187°-188° C.; UV: $\epsilon_{240} = 14000$; $[\alpha]_D = +13°$ (c=1% in dioxane); and from 6α,9α-difluoro-11β,17aα-dihydroxy-D-homopregna-1,4-diene-3,20-dione there was obtained 17aα-butyryloxy-6α,9α-difluoro-11β-hydroxy-D-homopregna-1,4-diene-3,20-dione of melting point 224°-225° C.; UV: $\epsilon_{238} = 16400$; $[\alpha]_D = +14°$ (c=0.1% in dioxane).

EXAMPLE 18

In analogy to Examples 14–16, from 6α-fluoro-11β,17aα-dihydroxy-D-homopregna-1,4-diene-3,20-dione there was obtained 17aα-butyryloxy-6α-fluoro-11β-hydroxy-D-homopregna-1,4-diene-3,20-dione of melting point 168°-169° C.; UV: $\epsilon_{242} = 16600$; $[\alpha]_D = +13°$ (c=0.1% in dioxane).

EXAMPLE 19

If, in Example 15, there is used acetic acid, propionic acid or valeric acid in place of butyric acid, then there are obtained from 9α-fluoro-11β,17aα-dihydroxy-D-homopregna-1,4-diene-3,20-dione in analogy to Examples 14-16 17aα-acetoxy-9α-fluoro-11β-hydroxy-D-homopregna-1,4-diene-3,20-dione of melting point 232°-233° C.; UV: $\epsilon_{239}=13900$; $[\alpha]_D = +29°$ (c=0.1% in dioxane); 9α-fluoro-11β-hydroxy-17aα-propionyloxy-D-homopregna-1,4-diene-3,20-dione of melting point 204°-205° C.; UV: $\epsilon_{238}=15100$; $[\alpha]_D = +23°$ (c=0.1% in dioxane); and 9α-fluoro-11β-hydroxy-17aα-valeroyloxy-D-homopregna-1,4-diene-3,20-dione of melting point 144°-146° C.; UV: $\epsilon_{239}=15400$; $[\alpha]_D = +17°$ (c=0.1% in dioxane).

EXAMPLE 20

300 mg. of 11β,17aα-dihydroxy-6-methylene-D-homopregn-4-ene-3,20-dione, 150 mg. of 5% palladium/carbon, 1.5 ml. of cyclohexene and 15 ml. of ethanol were boiled at reflux for 8.5 hours under argon. The mixture was cooled to 25° C., treated with 0.75 ml. of 25% hydrochloric acid and stirred for 1 hour. The catalyst was filtered off and the filtrate evaporated. Chromatography on silica gel gave 11β,17aα-dihydroxy-6α-methyl-D-homopregn-4-ene-3,20-dione of melting point 223°-225° C.; UV: $\epsilon_{242}=14100$; $[\alpha]_D = +46°$ (c=0.1% in dioxane).

The starting material can be prepared as follows:

11β,17aα-dihydroxy-D-homopregn-4-ene-3,20-dione is reacted in boiling methanol with pyrrolidine to give 11β,17aα-dihydroxy-3-(1-pyrrolidinyl)-D-homopregna-3,5-dien-20-one. This is reacted with formalin in benzene and methanol to give 11β,17aα-dihydroxy-6β-hydroxymethyl-D-homopregn-4-ene-3,20-dione. Treatment with hydrochloric acid in dioxane gives 11β,17aα-dihydroxy-6-methylene-D-homopregn-4-ene-3,20-dione.

EXAMPLE 21

A 2-liter Erlenmeyer flask containing 500 ml. of nutrient solution (sterilized for 30 minutes at 120° C. in an autoclave) comprising 1% cornsteep liquor, 1% soya powder and 0.005% soya oil, adjusted to pH 6.2, is inoculated with a lyophilized culture of Curvularia lunata (NRRL 2380) and shaken on a rotary shaker at 30° C. for 72 hours. A 20-liter stainless steel fermenter containing 15 liters of a medium (sterilized at 121° C. and 1.1 atmospheres) comprising 1% cornsteep liquor, 0.5% starch sugar and 0.005% soya oil, adjusted to pH 6.2, is then inoculated with the aforementioned pre-culture. Cultivation is carried out for 24 hours at 29° C. with aeration (10 liters/minute), at 0.7 atmospheres and while stirring (220 revolutions/minute) with the addition of a silicon oil (Silicon SH) as an anti-foam agent. 1 liter of the culture broth is transferred under sterile conditions into 14 liters of a medium (sterilized as described earlier) comprising 1% cornsteep liquor, 1.25% soya powder and 0.005% soya oil and cultivated under the same conditions. After 12 hours, there is added a solution of 4 g. of 17aα-actoxy-D-homo-4-pregnene-3,20-dione in 100 ml. of dimethylformamide. After 52 hours, the content of the fermenter is extracted twice by stirring with 10 liters of methyl isobutyl ketone and theextract evaporated at 50° C. (bath temperature) in vacuo. In order to remove the silicon oil, the residue is washed several times with hexane and separated from unreacted starting material by column chromatography on silica gel [gradient elution: hexane+hexane/ethyl acetate 1+(1/1)]. The 17aα-acetoxy-11β-hydroxy-D-homo-4-pregnene-3,20-dione is recrystallized from isopropyl ether; melting point 234°-235°-237° C.; $\epsilon_{242}=16700$.

EXAMPLE 22

A 2-liter Erlenmeyer flask containing 500 ml. of a nutrient solution (sterilized for 30 minutes at 120° C. in an autoclave) comprising 1.5% peptone, 1.2% cornsteep and 0.2% magnesium sulfate, adjusted to pH 6.5, is inoculated with a lyophilized culture of Bacillus lentus (ATCC 13805) and shaken at 30° C. for 24 hours. A 20-liter stainless steel fermenter containing 15 liters of a liquid nutrient medium (sterilized at 121° C. and 1.1 atmospheres) comprising 0.2% yeast extract, 1% cornsteep liquor and 0.1% starch sugar, adjusted to pH 7.0, is then inoculated with the aforementioned pre-culture. Cultivation is carried out at 29° C. with aeration and stirring and with the addition of a silicon oil (Silicon SH) as an anti-foam agent. After a growth-phase of 6 hours, there is added a solution of 1.6 g. of 17aα-acetoxy-11β-hydroxy-D-homo-4-pregnene-3,20-dione in 50 ml. of dimethylformamide. After 15 hours, the content of the fermenter is extracted twice with 10 liters of methyl isobutyl ketone and the extract evaporated in vacuo. In order to remove the silicon oil, the residue is washed with hexane and recrystallized from acetone/diisopropyl ether in the presence of active carbon, there being obtained 17aα-acetoxy-11β-hydroxy-D-homo-1,4-pregnadiene-3,20-dione of melting point 218°/219°=220° C. and $\epsilon_{244}=15100$.

The following Example illustrates a pharmaceutical preparation provided by the present invention and the manufacture thereof:

EXAMPLE A

The D-homopregnanes of formula I' can be made up, for example, in the form of salves as follows:

| | |
|---|---|
| D-Homopregnane | 0.01-1 wt. % |
| Liquid paraffin | 10.0 wt. % |
| White soft paraffin ad | 100 parts by weight |

The D-homopregnane is ground with a portion of the liquid paraffin in a ball mill until a particle size of less than 5μ is achieved. The paste is diluted and the mill washed out with the remaining liquid paraffin. The suspension is added to the molten colorless soft paraffin at 50° C. and stirred until the mass is cold, there being obtained a homogeneous salve.

We claim:

1. A D-homopregnane of the formula

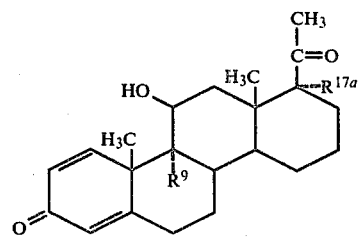

wherein $R^9$ is hydrogen or fluoro; and $R^{17a}$ is alkanoyloxy of 1 to 7 carbon atoms with the proviso that the C-11 hydroxy group is β-oriented when $R^9$ is hydrogen.

2. A compound according to claim 1 which is 17aα-butyryloxy-11β-hydroxy-D-homopregna-1,4-diene-3,20-dione.

3. A compound according to claim 1 which is 17aα-butyryloxy-9α-fluoro-11β-hydroxy-D-homopregna-1,4-diene-3,20-dione.

4. A topical anti-inflammatory pharmaceutical composition comprising a compatible pharmaceutical carrier material and as the active ingredient an amount of a D-homopregnane of the formula

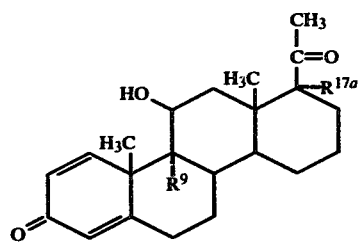

wherein $R^9$ is hydrogen or fluoro; and $R^{17a}$ is alkanoyloxy of 1 to 7 carbon atoms with the proviso that the C-11 hydroxy group is β-oriented when $R^9$ is hydrogen.

5. A topical anti-inflammatory pharmaceutical composition according to claim 4 wherein the D-homopregnane is 17aα-butyloxy-11β-hydroxy-D-homopregna-1,4-diene-3,20-dione.

6. A topical anti-inflammatory pharmaceutical composition according to claim 4 wherein the D-homopregnane is 17aα-butyryloxy-9α-fluoro-11β-hydroxy-D-homopregna-1,4-diene-3,20-dione.

7. A systemic anti-inflammatory pharmaceutical composition according to claim 4 wherein the amount of D-homopregnane is effective as an anti-inflammatory agent is about 0.05 to 10.0 mg. per day.

8. A topical anti-inflammatory pharmaceutical composition according to claim 4 wherein the amount of D-homopregnane is effective as an anti-inflammatory agent is in the range of from about 0.0001 weight percent to about 5 weight percent.

9. A composition according to claim 8 wherein the amount of D-homopregnane is effective as an anti-inflammatory agent is in the range of from about 0.001 weight percent to about 0.5 weight percent.

10. A composition according to claim 9 wherein the amount of D-homopregnane is effective as an anti-inflammatory agent is in the range of from about 0.01 weight percent to about 0.25 weight percent.

* * * * *